(12) United States Patent
Bruce et al.

(10) Patent No.: US 6,514,704 B2
(45) Date of Patent: Feb. 4, 2003

(54) QUALITY CONTROL MECHANISM AND PROCESS FOR A BIOFLUID MULTI-EJECTOR SYSTEM

(75) Inventors: Richard H. Bruce, Los Altos, CA (US); Scott A. Elrod, La Honda, CA (US); Babur B. Hadimioglu, Mountain View, CA (US); David A. Horine, Los Altos, CA (US); Jaan Noolandi, Mississauga (CA); Joy Roy, San Jose, CA (US); Robert A. Sprague, Saratoga, CA (US)

(73) Assignee: Xerox Corporation, Stamford, CT (US)

( * ) Notice: Subject to any disclaimer, the term of this patent is extended or adjusted under 35 U.S.C. 154(b) by 0 days.

(21) Appl. No.: 09/773,804

(22) Filed: Feb. 1, 2001

(65) Prior Publication Data

US 2002/0102555 A1 Aug. 1, 2002

(51) Int. Cl.⁷ .................................................. C12Q 1/68
(52) U.S. Cl. ........................ 435/6; 435/91.1; 435/91.2; 536/23.1; 324/204; 324/232; 324/226; 324/262
(58) Field of Search .......................... 435/6, 91.1, 91.2; 324/204, 232, 226, 262; 536/23.1

(56) References Cited

U.S. PATENT DOCUMENTS 5,583,432 A * 12/1996 Barnes

* cited by examiner

*Primary Examiner*—W. Gary Jones
*Assistant Examiner*—Janell E. Taylor
(74) *Attorney, Agent, or Firm*—Fay, Sharpe, Fagan, Minnich & McKee, LLP (57) ABSTRACT

A method and mechanism for ensuring quality control in printed biological assays is provided. A multi-ejector system having a plurality of individual drop ejectors is loaded with a variety of biofluids. Biofluids include at least a carrier fluid, a biological material to be used in the testing, and markers, such as fluorescent dyes. Data regarding the biofluid loaded in each of the drop ejectors is stored along with an expected signature output of the biofluid. Particularly, the signature output represents signals from individual ones of the fluorescent markers included within the biofluid. Once a biological assay consisting of the biofluid drops has been printed, a scanner capable of detecting the markers scans the biological assay and obtains signature output signals for each of the drops of the biological assay. A comparing operation is undertaken to compare the obtained signature output through the scanning operation, with the expected signature output signals for the biofluid loaded in the corresponding drop ejector. The biological material itself may also be tagged with a marker to ensure its inclusion in the biofluid. By the comparing operation, it is possible to verify the biofluids were loaded in the proper drop ejector, including the proper biological material, and that the drop ejectors are functioning properly.

12 Claims, 13 Drawing Sheets

|   | FLUORESCENT | ABSORPTION | FLUORESCENT EMISSION |
|---|---|---|---|
| A | ALEXA FLUOR 350 | 346 | 442 |
| B | ALEXA FLUOR 430 | 433 | 539 |
| C | ALEXA FLUOR 488 | 495 | 519 |
| D | ALEXA FLUOR 532 | 532 | 554 |
| E | ALEXA FLUOR 546 | 556 | 573 |
| F | ALEXA FLUOR 568 | 578 | 603 |
| G | ALEXA FLUOR 594 | 590 | 617 |
| H | ALEXA FLUOR 633 | 632 | 647 |
| I | ALEXA FLUOR 660 | 663 | 690 |
| J | ALEXA FLUOR 680 | 679 | 702 |

|     | A1 | A2 | A3 | A4 | An |
| --- | --- | --- | --- | --- | --- |
| FL1 | 1 | 0 | 0 | 0 | 1 |
| FL2 | 1 | 1 | 0 | 0 | 0 |
| FL3 | 1 | 1 | 1 | 0 | 0 |
| FL4 | 0 | 1 | 1 | 1 | 0 |
| FL5 | 0 | 0 | 1 | 1 | 1 |
| FL6 | 0 | 0 | 0 | 1 | 1 |

*FIG. 17*

|     | B1 | B2 | B3 | B4 | Bn |
| --- | --- | --- | --- | --- | --- |
| FL1 | 1/2 | 0 | 0 | 0 | 1/2 |
| FL2 | 1 | 0 | 0 | 0 | 0 |
| FL3 | 1/2 | 1/2 | 1/2 | 0 | 0 |
| FL4 | 0 | 1/2 | 1 | 1/2 | 0 |
| FL5 | 0 | 0 | 1 | 1/2 | 1/2 |
| FL6 | 0 | 1 | 0 | 1/2 | 1/2 |

QUALITY CONTROL MECHANISM AND PROCESS FOR A BIOFLUID MULTI-EJECTOR SYSTEM

BACKGROUND OF THE INVENTION

The present invention is directed to a quality control mechanism and process in a multi-ejector system, and more particularly, to ensuring the quality of a printed biological assay consisting of a plurality of biofluid drops ejected by the multi-ejector system.

Many scientific tests such as those directed to biology, genetics, pharmacology and medicine, employ sequences or arrays of biofluid drops on which the tests are to be performed. In some testing applications up to several thousand biofluid drops can be deposited onto a single substrate where a single substrate contains a variety of unique known biofluids. For example, in current biological testing for genetic defects and other biochemical aberrations, thousands of the individual biofluids may be placed on a substrate. Thereafter, additional biofluids are deposited on the previously deposited drops to initiate interactions. This treated biological assay is then scanned in order to observe changes in physical properties of the fluids.

If the biological assay is defective, testing undertaken with the biological assay is invalid, resulting in false and potentially dangerous consequences. It is therefore critical the biological assay has the appropriate biofluid deposited at the appropriate locations, in appropriate amounts.

Quality control mechanisms and processes are not now available which provide the high quality assurance for large-drop assays, in an economical manner.

SUMMARY OF THE INVENTION

A method and mechanism for ensuring quality control in printed biological assays is provided. A multi-ejector system having a plurality of individual drop ejectors is loaded with a variety of biofluids. The biofluids include at least a carrier fluid, a biological material to be used in the testing, and markers, such as fluorescent dyes. Data regarding the biofluid loaded in each of the drop ejectors is stored along with an expected signature output of the biofluid. Particularly, the signature output represents signals from individual ones of the fluorescent markers included within the biofluid. Once a biological assay consisting of the biofluid drops has been printed, a scanner capable of detecting the markers scans the biological assay and obtains actual signature output signals for each of the drops of the biological assay. A comparing operation is undertaken to compare the obtained signature output through the scanning operation, with the expected signature output signals for the biofluid loaded in the corresponding drop ejector. The biological material itself may also be tagged with a marker to ensure its inclusion in the biofluid. Implementation of the comparing operation makes it possible to verify the biofluids were loaded in the proper drop ejector, including the proper biological material, and that the drop ejectors are functioning properly.

DETAILED DESCRIPTION OF PREFERRED EMBODIMENTS

Figure 1:
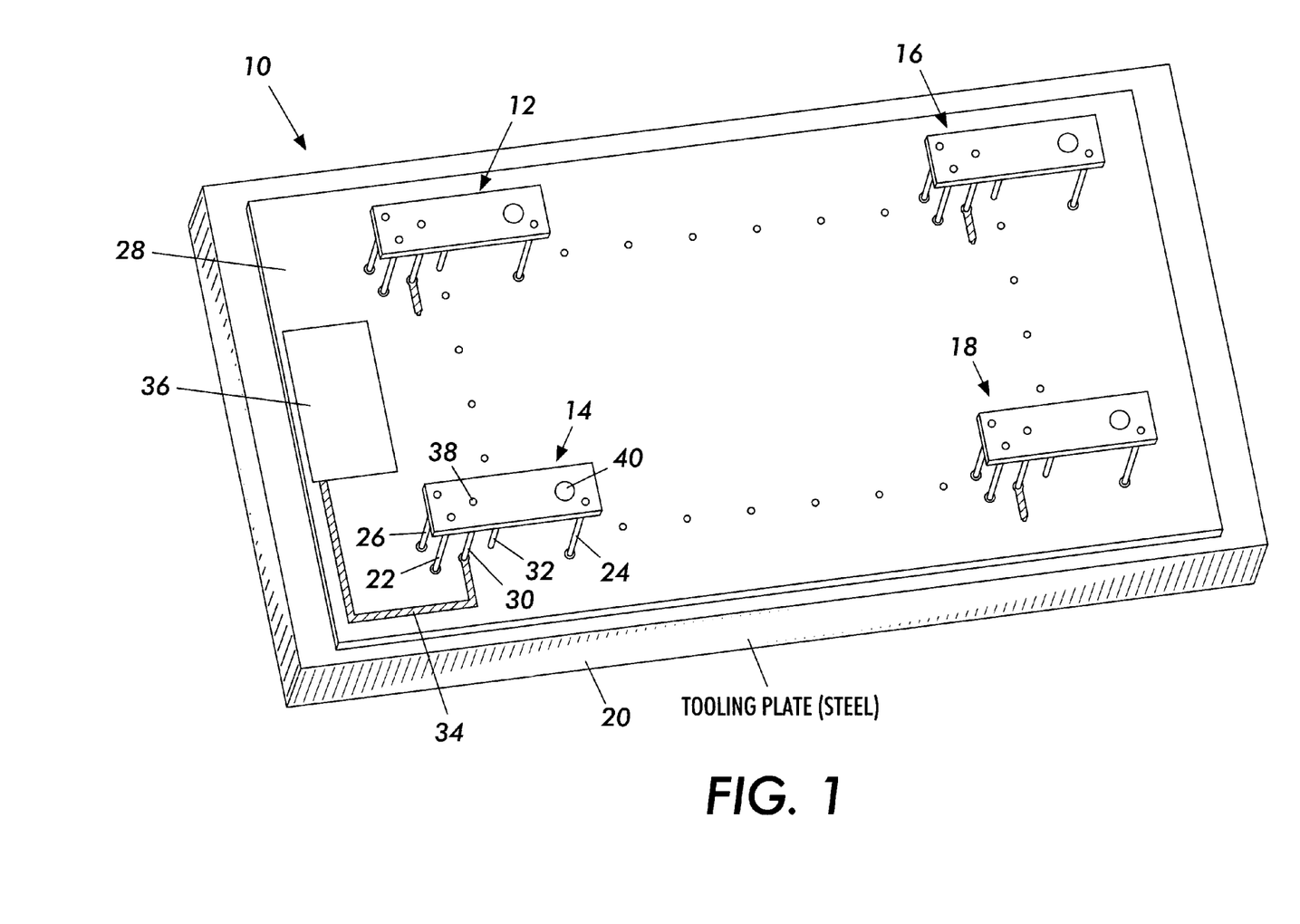
FIG. 1 illustrates a multiple ejector system which may implement either single or two drop ejection mechanisms.

FIG. 1 illustrates a multiple ejector system (MES) 10 which permits the printing of high density biological assays. Multiple ejector system 10 of this embodiment consists of an array having 10 rows, where each row includes 100 drop ejector units. Particularly, in this embodiment drop ejector unit 12 may be considered a first ejector in a first row. Drop ejector 14 is the $100^{th}$ ejector in the first row, ejector 16 is the first ejector in the $10^{th}$ row and ejector 18 is the $100^{th}$ ejector in the $10^{th}$ row. For convenience, only selected ones of the 1,000 ejectors of this array are shown. It is to be understood that multiple ejector systems having different numbers of ejectors will also benefit from the concepts of the present invention.

Drop ejectors which of multiple ejector system 10 may be any of a variety of ejectors which allow for high-density drop ejection. For example, such drop ejectors would include a single-piece piezoelectric drop ejector, a single-piece acoustic drop ejector, a two-piece piezoelectric drop ejector, as well as a two-piece acoustic drop ejector. Specific designs which may be implemented in various embodiments of the present invention have been taught in previously filed patent applications including U.S. application Ser. No. 09/718,733, filed Nov. 22, 2000, entitled: Testing Methods And Configurations For Multi-Ejector System; U.S. application Ser. No. 09/724,987, filed Nov. 22, 2000, entitled: Devices For Biofluid Drop Ejection; and U.S. patent application Ser. No. 09/721,386, filed Nov. 22, 2000, entitled: Level Sense And Control System For Biofluid Drop Ejection Devices, each assigned to the present assignee and each hereby incorporated by reference.

The described biofluid drop ejection units function using small amounts of biofluid. For example, in one embodiment the ejector includes a main reservoir which, when full, contains anywhere from 50–150 microliters of biofluid, and an ejection is reservoir, which when full, holds anywhere from 5–25 microliters. Thus, operation of the drop ejection units may be accomplished using very low volumes of biofluid. The biofluid drops themselves may be in the picoliter range, and such ejectors would have tolerances of between +/−20 to +/−30% accuracy as to drop volume. The small volume of the biofluid drops ejected, is a beneficial aspect of the drop ejection units due to the high cost of many of the biofluids which will be used. Also, since very small volumes of biofluid are required, the use of disposable ejector units become an attractive option.

It is to be appreciated that the described drop ejection units also operate at a high efficiency whereby little waste of the biofluids will occur. This is due both to the operational aspects of the units themselves and to the fact that only small volumes of biofluid are necessary to operate the units. Particularly, if any waste does exist within the system, due to the small amount of biofluid originally used, high efficiencies in operation are nevertheless achievable. In one preferred embodiment, high efficiency is defined as use of 80% or more of the biofluid under normal operation.

While the foregoing discussion stated that there would be 50–150 microliters in the main reservoir, and 5–25 microliters in the ejection reservoir, these amounts may vary dependent upon the drop size being used, the amount of printing to be undertaken, the types of biofluids to be used, as well as other parameters.

Returning to the configuration of MES 10, shown is a tooling plate 20 which has machined therein sets of conical-tip tooling pins 22, 24 and 26. These tooling pins are precisely manufactured into the tooling plate to selectively engage the drop ejectors (e.g. ejectors 12–18). Use of tooling pins 22–26 ensures appropriate registration of the nozzle of the piezoelectric drop ejection units or the aperture of the acoustic drop ejection units. It is to be appreciated that drop ejection units 12–18 are intended to represent either piezoelectric drop ejection units, acoustic drop ejection units or other appropriate drop ejectors.

Tooling plate 20 may be made of steel or other appropriate material. Placed on a top surface of tooling plate 20 is a printed circuit (PC) board 28. Extending from the surface of PC board 28, are power connection pin 30 and a ground return connection pin 32. The connection pins 30 and 32 engage the drop ejection unit 14 on one end and the PC board 28 on a second end. Additionally, power connection pin 30 is further connected to an electrical trace 34 located on the PC board 28, which in turn connects to a controller or driver chip 36. The controller or driver chip 36 selectively supplies power to drop ejection unit 14 via electrical trace 34 and power connection pin 30. As will be discussed in greater detail below, this selective application of power is used to operate drop ejection unit 14.

As shown, drop ejection unit 14 will include either a nozzle or aperture 38, dependent upon whether the mechanism is a piezoelectric drop ejection unit or an acoustic drop ejection unit or other ejector type. A fill port 40 is provided for the receipt of a biofluid used to print the biological assay. The ejectors may be loaded by a loading mechanism 41, shown in dashed lines. It is to be appreciated while loading may occur on-site a preferred embodiment is to have loading mechanism 41 load the ejectors off-site and then have the loaded ejectors place into the system. It is also to be understood that different biofluids will be placed in different ejectors of the MES 10. By proper placement of the tooling pins 22–26, and the placement of the alignment grooves or openings of the ejectors, overall placement of individual drop ejector units with the system 10 may be ensured to within a thousandth of an inch of an ideal location.

Figure 2:
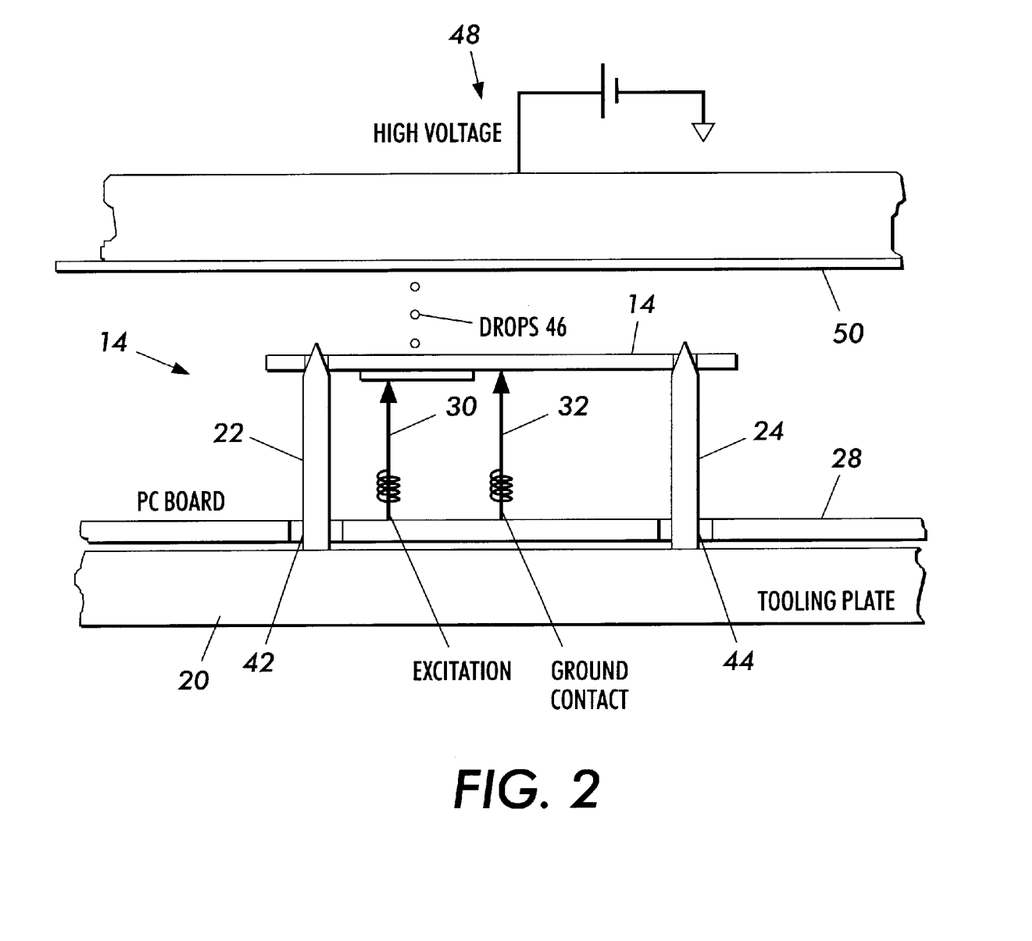
FIG. 2 sets forth a side view of a multiple ejector system illustrating a single ejector, single piece mechanism.

Turning to FIG. 2, illustrated is a side view of a single drop ejection unit 14 of MES 10. Tooling plate 20 includes the tooling pins 22 and 24 previously described. Pin 26 cannot be viewed in this figure, as it is located behind pin 22. On top of tooling plate 20 is PC board 28 having through holes 42 and 44. A further throughhole for pin 26 would also be provided. As shown more clearly in this figure, connection pins 30 and 32 extend from the surface of PC board 28 to engagement at appropriate locations of drop ejection unit 14. For example, connection pin 30 which receives power from controller 36, operationally engages the transducer of either the piezoelectric or acoustic drop ejection unit. Supplying power activates the drop ejection unit 14 causing emission of drops 46. A ground contact is achieved by use of connection pin 32. Both connection pins 30 and 32 may be designed as pogo pins which are a spring-loaded mechanisms. Thus when drop ejection unit 14 is located over tooling pins 22, 24, 26 and is pressed downward such that pins 22–26 pass through corresponding alignment holes, spring engagement is made between connection pins 30, 32 and drop ejection unit 14 providing the electrical contacts described.

A static voltage 48 may be placed on the backside of substrate 50 to counter the affects of gravity and viscous drag on drops 46, which act to move drops out of a straight path to the substrate. Use of static voltage 48 increases the accuracy with which drops 46 are placed on substrate 50, by providing a strong attraction force. The flight of the drops are an important concept as small misregistrations can cause cross-contamination between drops or misreadings of the biological assay once developed.

Figure 3:
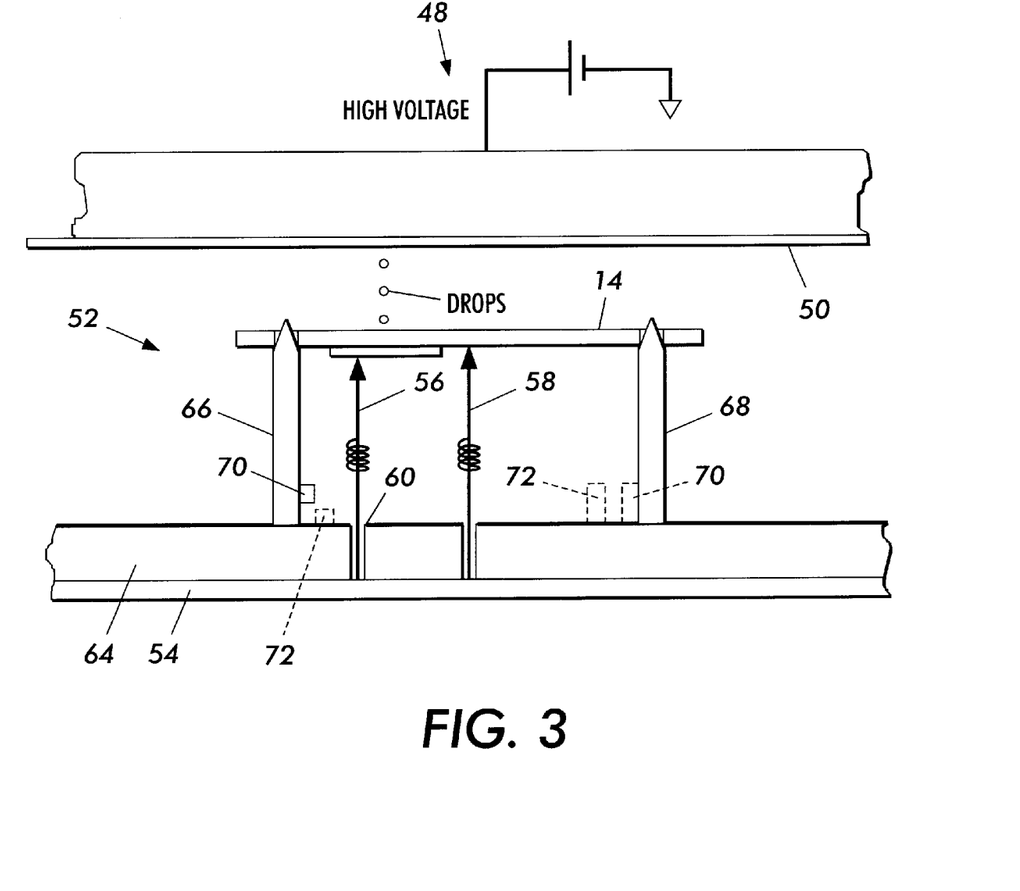
FIG. 3 sets forth a second embodiment of a multiple ejector system wherein shown is a single ejector.

FIG. 3, is a side view of a selected drop ejector 14 from an alternative multiple ejector system 52. In this embodiment circuit board 54 is the lowermost element of MES 52. Power connection pin 56 and ground return connection pin 58 are passed through openings 60 and 62 of tooling plate 64. It is to be noted that openings 60 and 62 need to be electrically isolated from pins 56 and 58. Similar to the previous discussion, tooling plate 64 has multiple sets of tooling pins 66 and 68 extending from the surface of tooling plate 64. A third tooling pin of the set, such as shown in FIG. 1 is also provided in FIG. 3 though not shown. Thereafter, drop ejection unit 14 is placed into engagement with tooling pins 66, 68 and connection pins 56, 58.

While the forgoing discussion has focused on tooling pins of FIGS. 2 and 3 as being conical pins on which the drop ejector 14 rests, in an alternative embodiment, these tooling pins may be designed simply to pass through the drop ejector and the drop ejector will move down until hitting predetermined stops located either extending from the pins themselves or from the tooling plate, such as stops 70 or 72, shown in dashed lines. Stops 70 and 72 are positioned such that proper alignment of the drop ejector is achieved. If this embodiment is undertaken, then tooling pins, such as 66 and 68 may be made much shorter in length. The shortening of the tooling pins are made shorter such that the portions of the pins passing through the drop ejector do not extend into the printing plane. In the embodiment shown in FIG. 3, the stops may also be provided by the PC board 166.

With attention to a further embodiment of the devices shown in FIGS. 2 and 3. While two connection or pogo pins 30, 32 in FIG. 2 and 56, 58 in FIG. 3, are shown to provide an excitation and a ground return, an embodiment with a single pogo pin may also be used. In the single pogo pin embodiment, the excitation pins 30 or 32 of FIGS. 2 and 3 will be maintained. However, the return or ground contact pogo pins 32 and 58 of FIGS. 2 and 3 may be replaced by providing the ground contact through use of the tooling pins interconnected to the alignment openings.

Multiple ejector systems 10, 52, may be considered applicable to single-piece drop ejection units. When these drop ejection units have been exhausted of biofluid, they may be removed from the tooling pins and replaced with new ejection units. Removal of the drop ejection units from the tooling pins may be accomplished by any of many known designs such as a snap-fit connection which is releasable upon application of an upward pressure.

Figure 4:
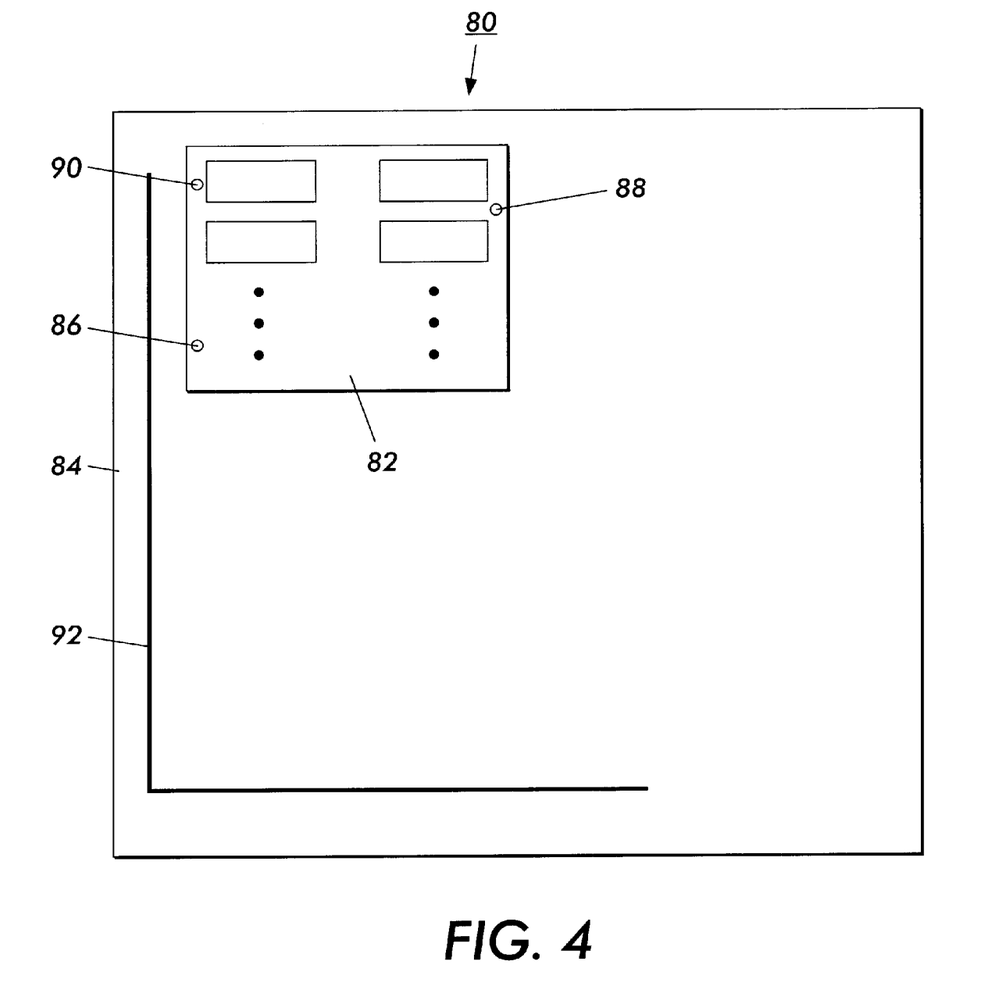
FIG. 4 depicts a front view of a multiple ejector system implementing sub-arrays of ejectors.

Turning to FIG. 4, illustrated is a top view of a further multiple ejector system 80. In this embodiment, rather than attaching individual drop ejection units, drop ejection sub-arrays, such as sub-array 82, are used. Specifically, multiple drop ejection units are configured on a single substrate 84, during for example, a drop ejection unit lithographic formation process. Using sub-arrays 82, requires fewer sets of tooling pins 86–90 on tooling plate 92. However, the same number of power connection and ground return connection pins as well as electrical tracings will be required. Additionally, using sub-arrays 82 increases the ease of handling the drop ejection units. Particularly, due to the small size of individual ejector units, handling these as individual units increases the complexity of the system as opposed to using the larger sub-arrays. Further, using the sub-arrays provides for more accurate alignment as a high degree of alignment accuracy may be obtained during the formation of the sub-array.

In order to increase the refinement of drop ejector position, connection pins such as those described in connection with FIGS. 2–4, are designed to have a certain flexibility built into the pin structure. This is beneficial, as this flexibility is useful for providing further fine alignment of the drop ejectors once connected to the pins. Thus, while the manufacturing process of the tooling plate and pins extending therefrom, as well as the connection holes on the drop ejectors are done with a high degree of precision, further alignment accuracy may be obtained if a spring or flexible capability is designed into the tooling pins. Such tooling pins allow for movement of the drop ejector in the horizontal X and Y plane such that the ejector is specifically aligned with a location for emitting. In an alternative embodiment, the through holes formed in the drop ejector units may be manufactured with a spring or flexible circumference, whereby firm engagement is made to the tooling pins, while also allowing for flexure in the X,Y horizontal range.

Further, the alignment grooves of the drop ejectors may be formed with a V groove or other design which allows for the movement of the pins for more precise alignment of the ejector. Such alignment elements and processings are known in the alignment field. Additionally, while the embodiments previously shown discuss the use of three pins in the set of pins holding a drop ejector unit. It is to be understood that other arrangements of pin sets are possible. For example, in the proper situation, a 2-pin, 4-pin or other pin set arrangement may be most appropriate.

FIGS. 2 and 3 illustrate multiple ejector systems which use single-piece drop ejection units, both for piezoelectric drop ejection mechanisms and acoustic drop ejection mechanisms or other types of ejectors. Turning to FIGS. 5–8, set forth are side views of a section of multiple ejector system arrangements for two-piece piezoelectric drop ejection mechanisms and two-piece acoustic drop ejection mechanisms.

Figure 5:
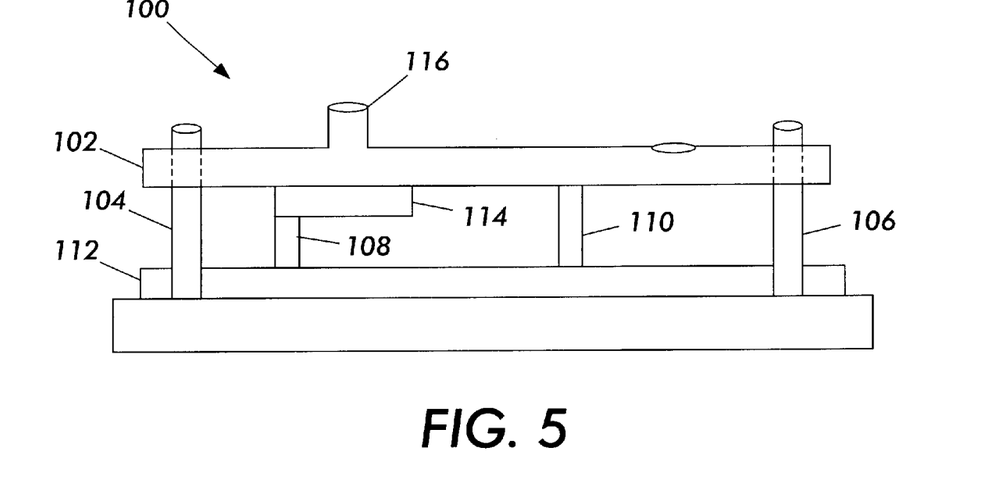
FIGS. 5 & 6 illustrate a single ejector in a multiple ejector system wherein the single ejector is a two-piece piezoelectric drop ejector unit.

FIG. 5 represents a side view of a multiple ejector system (MES) 100 and particularly a single ejector 102 of the system. Ejector 102 is connected to tooling pins 104 and 106. As in previous examples and for all following examples, there may also be at least one additional tooling pin, behind for example tooling pin 104, not seen in the figure. In this system 100 power connection pin 108 and ground return pin 110 extend from circuit board 112. Power connection pin 108 is in operative engagement with transducer 114, such that when power is supplied from a controller or driver chip to power pin 108 via electrical tracing, transducer 114 is activated causing ejection of droplets from nozzle 116.

Figure 6:
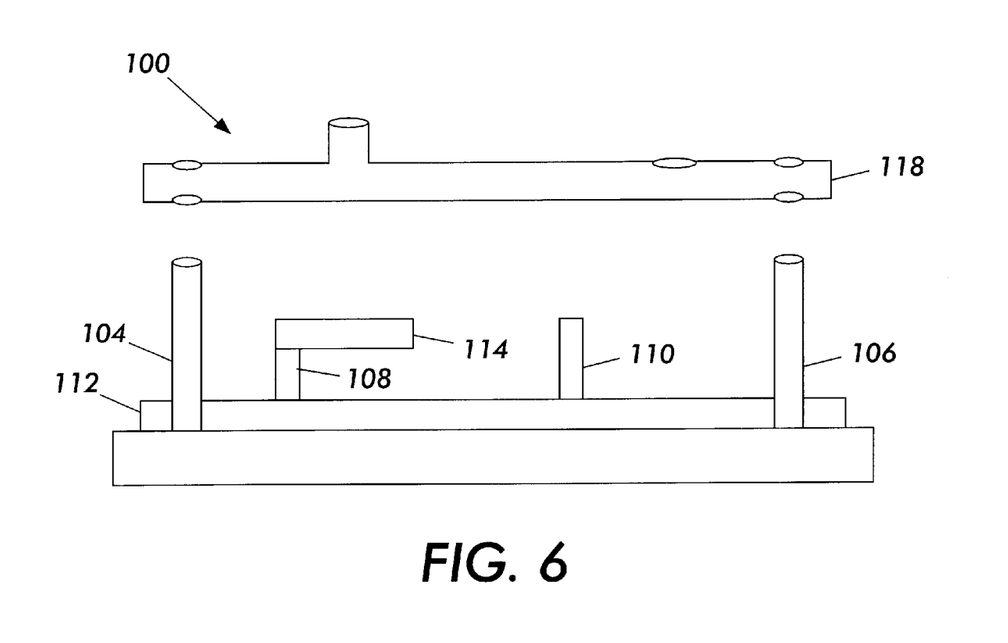

When the biofluid drop ejection unit of FIG. 5 is depleted, only the portion of the unit containing biofluid is removed. The transducer portion, as previously discussed, will be maintained in the system. FIG. 6 illustrates this removal. Biofluid holding portion 118 has been removed from tooling pins 104 and 106. The transducer 114 is maintained in contact with power connection pin 108. Therefore, the connection between power connection pin 108 and transducer element 114 is semi-permanent.

Figure 7:
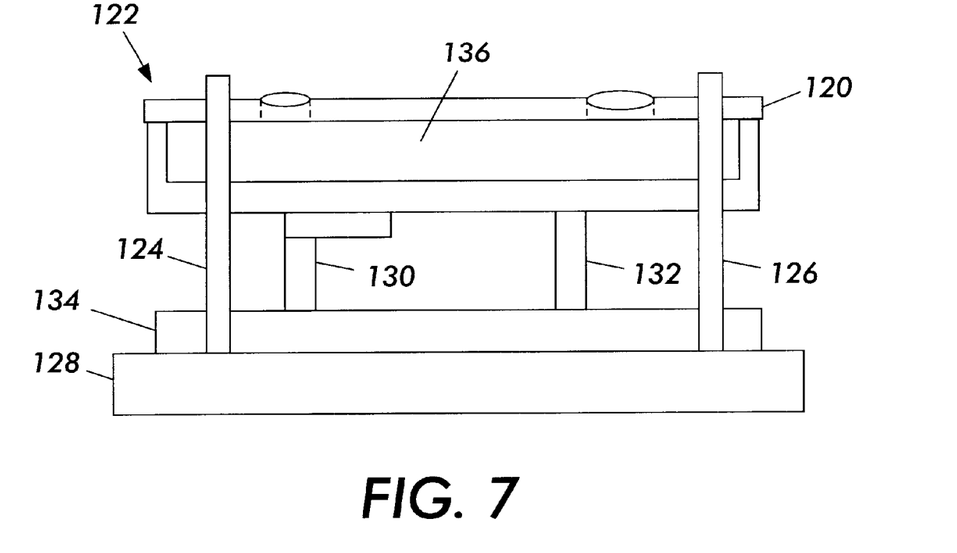
FIGS. 7 & 8 set forth a single ejector of a multiple ejector system wherein the ejector is a two-piece acoustic drop ejection mechanism.
Figure 8:
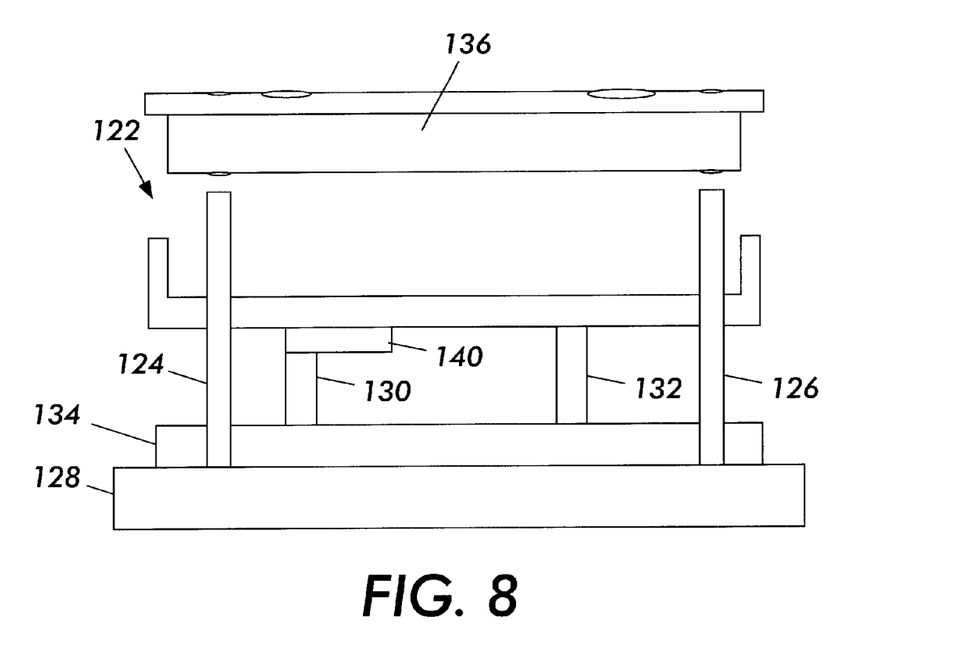

Turning to FIGS. 7 and 8, a configuration for a multiple ejection system 120 using two-piece acoustic drop ejection mechanisms is illustrated. In FIG. 7, drop ejection mechanism 122 is in operative connection with appropriate tooling pins 124, 126 of tooling plate 128, power connection pin 130 and ground return pin 132 of circuit board 134, such that it is ready for operation. Once the biofluid held in cartridge 136 has been depleted, cartridge 136 is removed. FIG. 8 illustrates this situation. Upon removal of cartridge 136, the remaining portion of the acoustic drop ejection mechanism 138 which includes transducer/lens arrangement 140, is maintained in engagement with connecting pins 270 and 132.

In FIGS. 5–8, after the original biofluid cartridge is removed replacement biofluid cartridges can then be inserted into the system. The insertion of these replacement biofluid cartridges or holders may be accomplished by use of robots. It is noted that the forgoing systems may all be implemented using the sub-arrays of FIG. 4. Further, the alternative embodiments discussed in connection with FIGS. 2–4 are equally applicable to the arrangements of FIGS. 5–8.

The multiple ejector system and components described in FIGS. 1–8 are used to generate biological assays which contain a biological material upon which hybridization or other testing is to be undertaken. In one embodiment the biofluids will contain DNA strands of a known type which are then to be tested against unknown DNA strands. A goal achieved by the multi-ejector systems of FIGS. 1–8 is high volume production of the biological assays at a low cost. Particularly, the high speed printing capabilities described by the foregoing systems permit a reduction in the costs involved in creating the biological assays which are to be used for further testing. The resulting lowered cost and economic viability removes one obstacle for increased use of such biological assays.

However, it is realized by the inventors that for such biological assays to be useful, reliability is of critical importance. Since the intent of multiple ejector systems is to create assays having from hundreds to thousands of individual biofluid drops in a small area, and to undertake such production at high speeds it is necessary to implement quality control mechanisms and processes to assure the correctness of the biofluids being deposited. Specifically, it is necessary to ensure the intended biofluid is located at the intended location on a substrate, and that such biofluid drop is of the proper size and form.

Since there will be a large number of different biofluids which may be used for a particular biological assay, it is important that there is an assurance the intended biofluid is located within the intended drop ejector. One particular manner of making sure biofluids within a MES are properly loaded, is to dope the biofluid of each drop ejector with at least one marker. Including markers in the biofluid of an ejector forms a unique fingerprint or signature for each ejector, such that when detected, the results are used to ensure the proper biofluid is being ejected from the proper ejector at the intended location.

Figure 9:
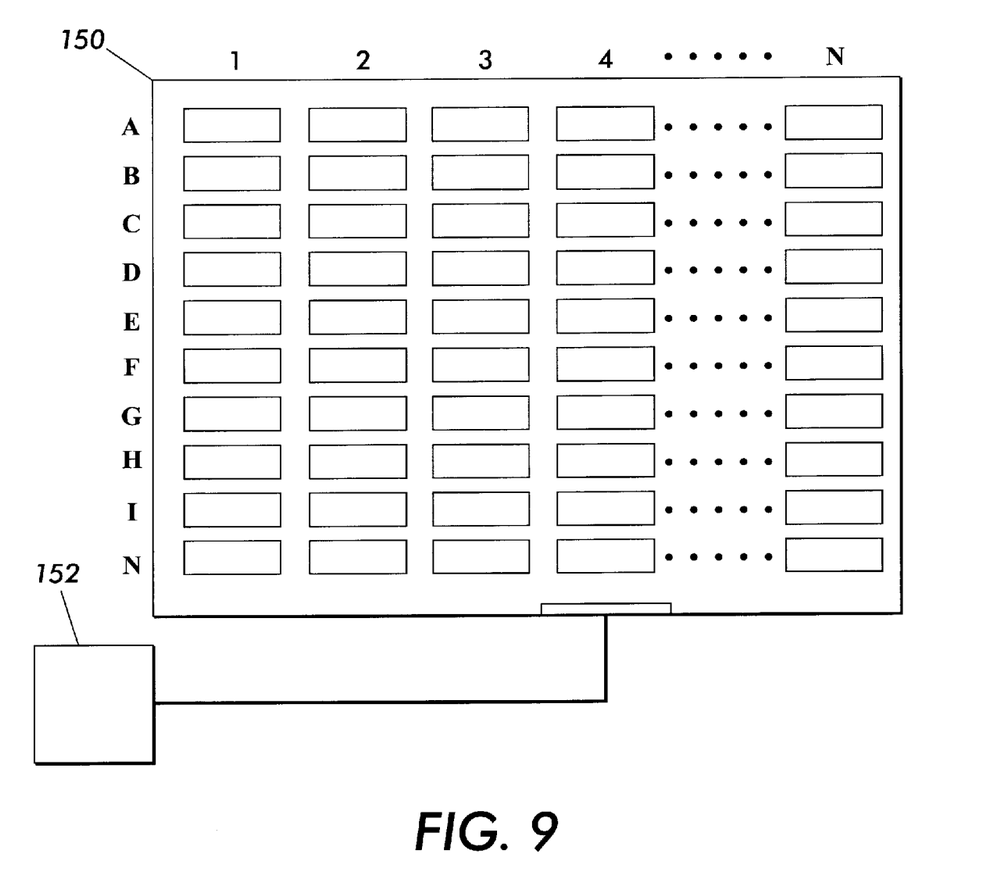
FIG. 9 depicts a configuration including the drop ejector printhead and controller.

Descriptions of how this doping scheme and operation may be achieved are set forth with the discussion accompanying FIGS. 9–19. With attention to FIG. 9, illustrated is a block diagram of a drop ejector printhead 150, and a printhead controller 152 which controls operation of the printhead. Each ejector on the printhead 150 is specifically defined. For example, ejector 154 may be defined as ejector A1, ejector 156 as A2, ejector 158 as A3 and so on. The designation and corresponding location of each ejector is stored by printhead controller 152. Controller 152 may be a separate computer system, or a controller chip located on printhead 150.

The drop ejectors are loaded with a particular biofluid which is to form the biofluid drops from that ejector. Along with the markers, the biofluid includes a carrier fluid and the biological material, such as single or duplex DNA strands, proteins or other material which is to be used for testing and experimentation purposes. The carrier fluid may be an inert buffer fluid into which is located the markers and biological material.

In operation, printhead controller 152 controls when an ejector is to function and eject this biofluid onto a substrate for a formation of the biological assay. However, it is understood that errors in the loading of the biofluid, loading of the biological material, or operation of the multiple ejector systems may occur. Therefore, quality control assurance mechanisms are used to ensure a high quality biological assay output.

In the present embodiment, the markers added to the biofluid are fluorescent dyes, used to track and confirm the proper placement of the biofluid, including that the intended biological material is located at the appropriate location in the appropriate amount. The created biological assay is scanned by an appropriate scanning device and the results verified against a standardized expected output to confirm the quality and accuracy of the generated biological assay.

More particularly, fluorescent dyes are known to generate known repeatable signature or fingerprint signals. One source of such dyes is from a Molecular Probes, Inc. of Eugene, Oreg. This company markets a series of fluorescent dyes under the registered trademark Alexa Fluor. When included in or added to other materials such as the carrier fluid or biological material (such as the single or duplex DNA strands) the dyes become absorbed. The approximate absorption and fluorescence emissions are known for the selected dyes.

Figure 10:
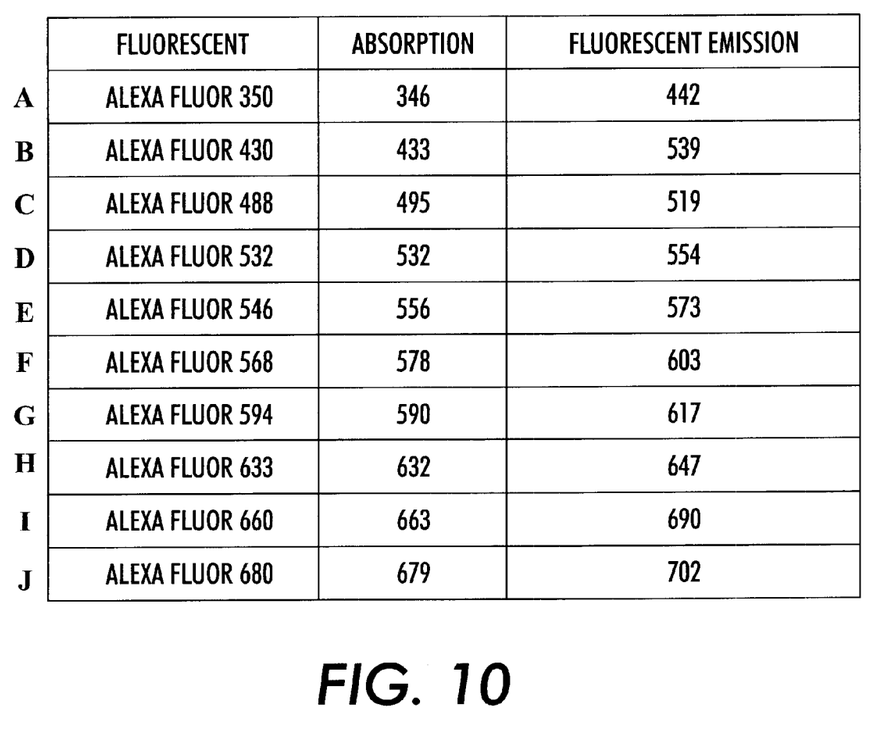
FIG. 10 illustrates a table of fluorescent markers which may be used in the present embodiment.
Figure 11:
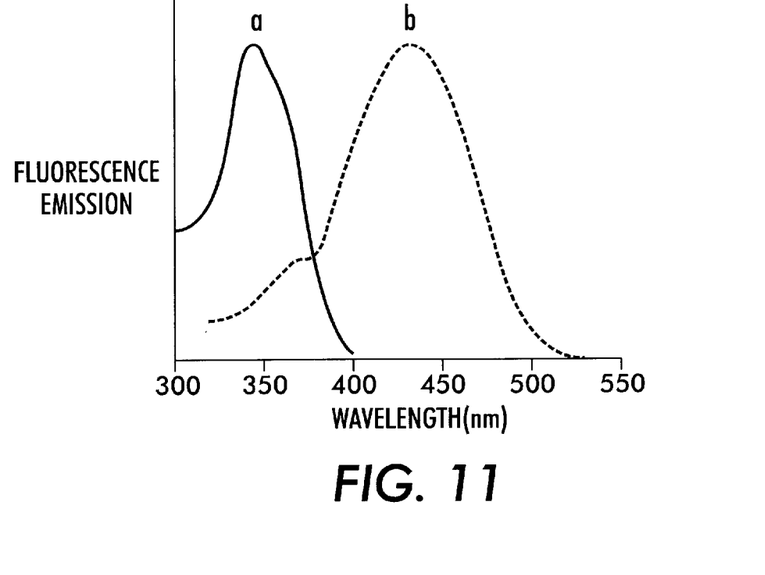
FIGS. 11–16 illustrate the absorption approximation output and the fluorescence emission for the markers of FIG. 10.
Figure 12:
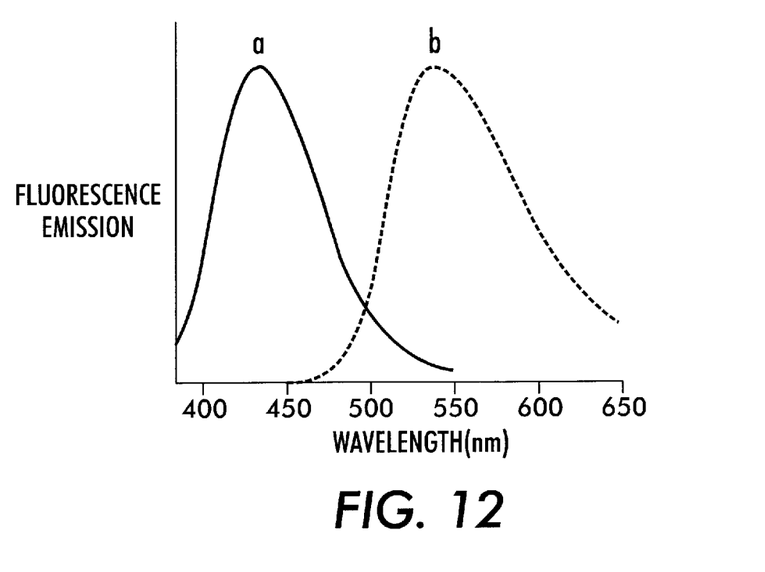
Figure 13:
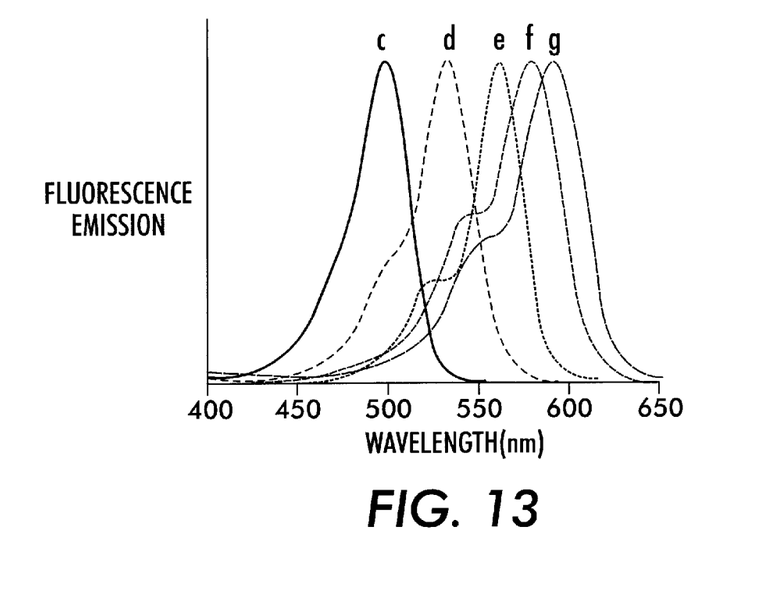
Figure 14:
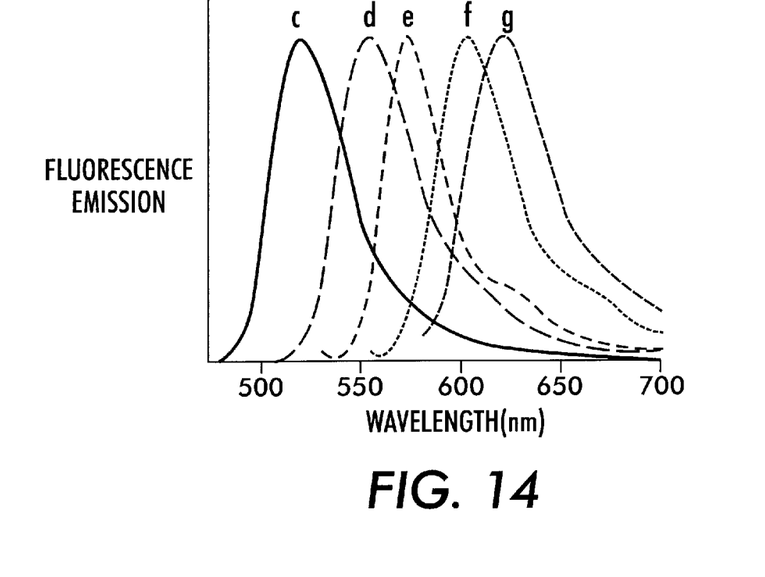
Figure 15:
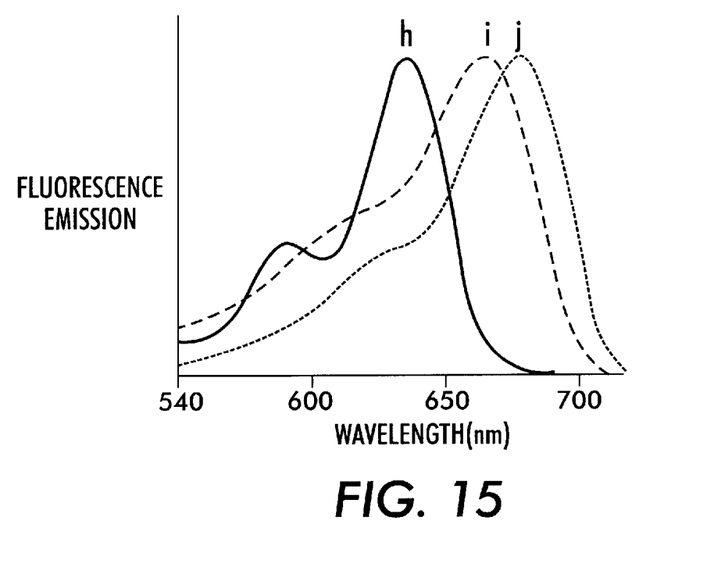
Figure 16:
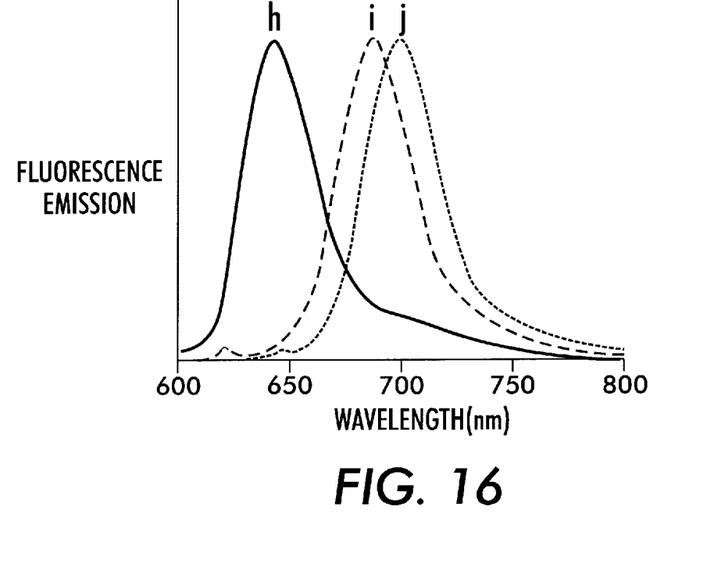

For example, FIG. 10 is a table listing a family of 10 Alexa Fluor dyes and their absorption approximation (Abs) and fluorescence emission (Em) maxima for conjugates, in nanometers. It is noted that for Alexa Fluor 633, 660 and 680, since human vision is insensitive to light beyond approximately 650 nanometers, it is not possible to view the far red fluorescent dyes simply through a conventional fluorescence microscope.

FIGS. 11–16 depict the absorption and fluorescence emission signals for the fluorescent dyes of FIG. 10. As illustrated by FIGS. 11–16, each dye will have a distinct peak emission output distinct from the other dyes. This distinct emission output is advantageously used in the quality assurance processes. It is also noted that these fluorescence dyes may work together for multi-labeling situations. Particularly, more than a single dye may be added to a biofluid, as the fluorescent dyes do not interact with each other. Therefore, it is possible to use a combination of dyes to provide each drop ejector with its unique detectable signature. It is to be appreciated, that while the fluorescent markers discussed have been those from Molecular Probes, Inc., other fluorescent markers may similarly be used with the present invention.

Figure 17:
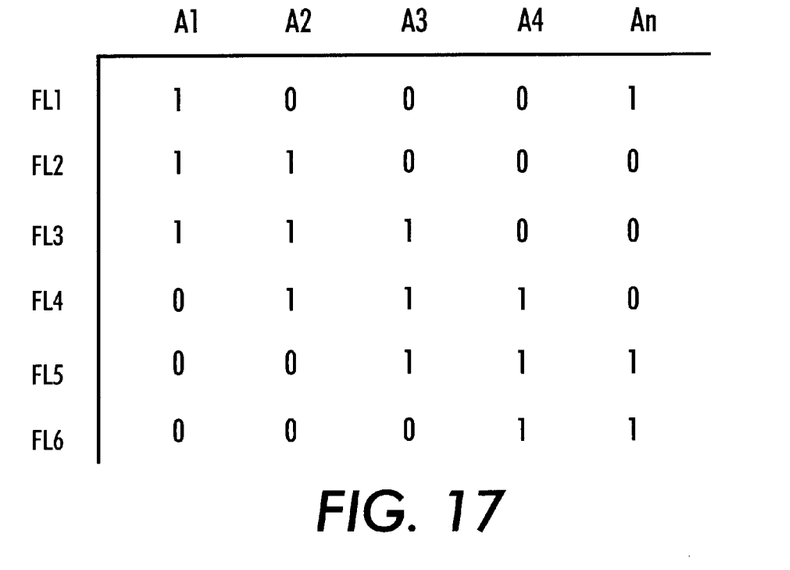
FIGS. 17 and 18 set forth exemplary tables of a combination of fluorescent markers which may be incorporated within the biofluid.

Turning to FIG. 17, shown is a table of potential combinations which would permit unique identification of the drop ejectors. In FIG. 17, the left hand column includes fluorescent dyes FL1–FL6. The ejectors under consideration are ejectors A1–AN of FIG. 9. For drop ejector A1, fluorescent dyes FL1, FL2 and FL3 are added to the biofluid to be loaded to this ejector. Whereas fluorescent dyes FL4, FL5 and FL6 are absent. As can be seen from the other columns of the table, the remaining ejectors A2–AN each have a unique combination of fluorescent dyes FL1–FL6. It is to be appreciated that a different number of fluorescent dyes may be used as well as different patterns or combinations.

Figure 18:
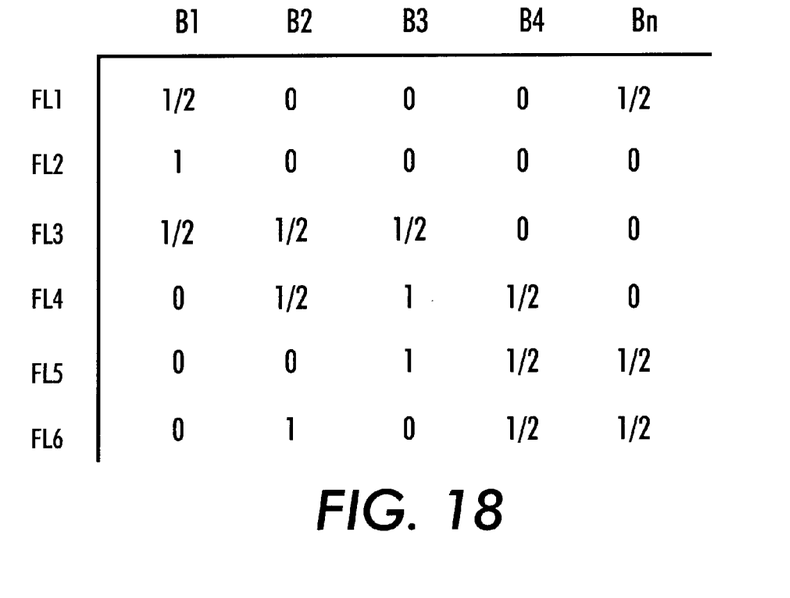

With further attention to providing a unique fingerprint or signature for each drop ejector and drop, attention is directed to FIG. 18. In this figure, it is noted that the fluorescent dyes are still FL1–FL6. However, now being considered are drop ejectors B1–BN. In this loading scheme, certain ones of the drop ejectors have only a half volume of a particular fluorescent marker. For example, for drop ejector B1, fluorescent dyes 1 and 3 (FL1 and FL3) are at a half volume amounts or intensity as compared to fluorescent marker 2 (FL2) also included in B1. Further, the pattern in B1–BN is different from the pattern of A1–An. The use of absent (0), half (½), and full (1) volumes of the fluorescent dyes increases the number of potential combinations, thereby permitting even a fewer number of dyes to account for each of the drop ejectors of a printhead. The loading of markers shown in FIGS. 17 and 18 are for explanatory purposes only, and the actual doping sequences will vary.

To obtain the half volume or intensity, tests determining the full volume, i.e. any selected value, and its corresponding signature output is obtained. Thereafter, only half that volume of a marker is added to determine the standard output signature or fingerprint for that particular fluorescent marker at the half value in the particular biofluid. Similar testing may be done for even more refined levels. For example, using equipment with sufficient sensitivity, ¼ volume levels or others may also be used.

Figure 19:
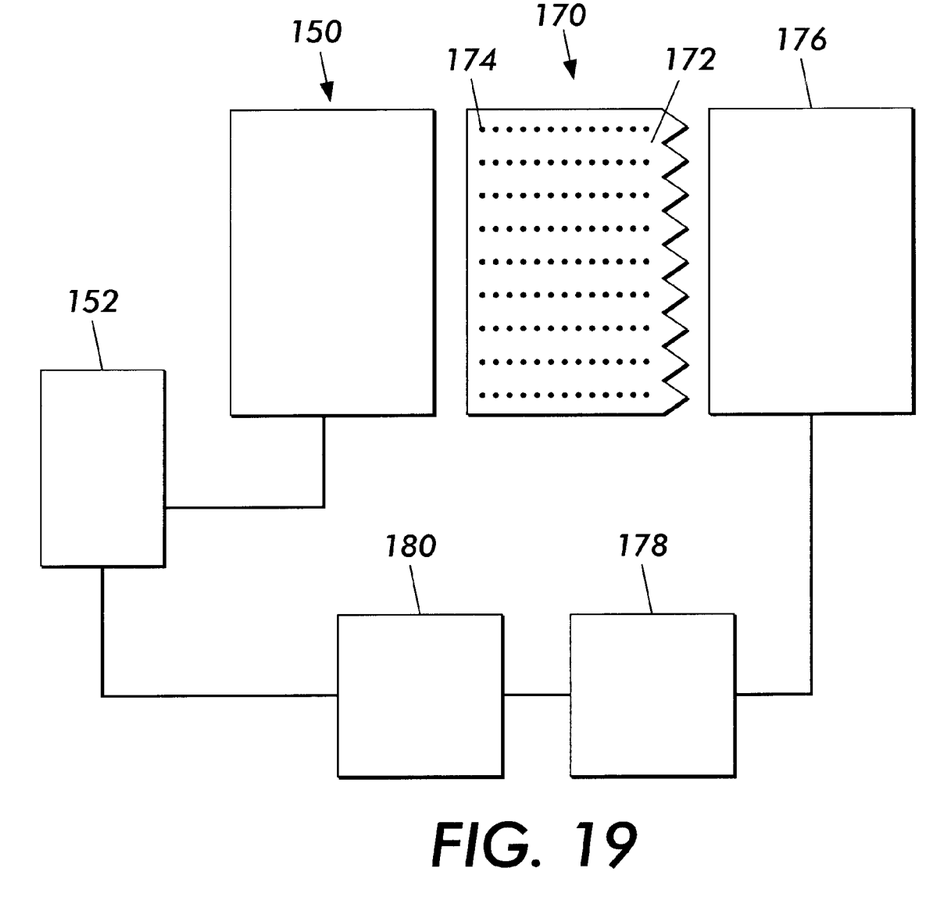
FIG. 19 sets forth an illustrative view including a scanner, controller and comparator which may be used in an embodiment of the present invention.

Once the drop ejectors are loaded with the biological material to be printed, the carrier fluid, and fluorescent dyes, the printing process is undertaken. As shown in FIG. 19, printhead 150 controlled by printhead controller 152 prints a biological assay 170 on a substrate 172 which may be a paper substrate, glass substrate, a substrate having a nylon membrane or other appropriate material. Each drop corresponds to at least some set of the drop ejectors. It is to be appreciated that not all drop ejectors may be emitting at the same time, and many varied and schemes of drop ejection may be used to achieve the output of the biological assay. However, in this embodiment for purposes of clarity, it will be assumed drop ejector A1 of printhead 150 has ejected drop 174 at position 1 (POS1).

The biological assay is passed through a scanner 176 capable of detecting the fluorescent dyes which have been included in the biofluid. A scanner controller 178 is provided to control operation of the scanner. It is to be appreciated that while scanner controller 178 is shown separate from scanner 176, it may be incorporated and made part of the scanner 176. Scanner 176 has the capability of detecting the wavelengths of the fluorescent dyes. One type of scanner which may be implemented in this embodiment is known as the 428™ Array Scanner from Affymetrix, Inc. of Santa Clara, Calif. This particular scanner has the ability to scan up to six different wavelengths in its detection of fluorescent dyes.

Once biological assay 170 is scanned, the detected information is provided to scanner controller 178. In this embodiment, scanner controller 178 will detect for example, that biofluid drop 174 at POS1 was detected to include a full volume (one unit) of FL1, FL2 and FL3. This information is then passed to a comparator 180. Comparator 180 is in operative connection with both scanner controller 178 and printhead controller 152. Information from controller 152 interprets that drop ejector A1 was responsible for dropping the drop located at position 1 (POS1). It is then interpreted that drop ejector A1 included a full volume (one unit) of FL1, FL2 and FL3 and that there is a correlation between the two. Thus, the comparing operation is used to verify that ejector (A1) ejected the intended biofluid at the intended location.

This comparing operation is continued for each drop on the biological assay 170. If it is determined that there is a match for each drop in comparison to the drop ejector functioning to produce that drop, then the biological assay is determined to pass the quality assurance test. If on the other hand, some nonconformity is determined in the comparing operation, the biological assay is tagged as defective and not accepted. The nonconformity determined by comparator 180 may be further investigated to determine whether there has been a mistake in the operation of the associated drop ejector, whether the wrong biofluid was loaded in the drop ejector, and/or the wrong biofluid information was stored in the controllers.

It is to be appreciated that in this embodiment, six fluorescent dyes are used, thereby allowing the use of the six frequency fluorescent scanner. In other embodiments, if more than six dyes are to be used, multiple scanners may be implemented or a scanner having the ability to determine more than six wavelengths could be used.

In another embodiment, markers, such as the fluorescent dyes may also be used to label, the biological material, such as the DNA probe. This embodiment acts as an assurance that the proper DNA or other biological material is loaded in the proper drop ejector. For example, in the proceeding embodiment, even if the fluorescent dye combination is matched as being accurate with the intended combination in the drop ejector, in instances where the biological material such as the DNA strands are added separately, there is the possibility the wrong biological material may be added to a drop ejector even if the drop ejector has the proper fluorescent dyes.

By adding a step of tagging the biological material with a marker, further quality assurance is obtained. Particularly, not only can the proper drop position, proper biofluid and proper ejector operation be confirmed, but it is also possible to confirm that the intended specific biological material was also ejected. More specifically, a marker, such as one of the fluorescent dyes, is tagged to a specific biological material, such as the DNA probe. The information regarding the unique marker attached to a specific DNA strand is stored in, for example, the printhead controller 152. The standardized expected output due to such a tagging would also be stored.

When the printed biological assay is scanned, the detected output emission values are compared to the standardized expected values in a manner similar to that for the markers in the carrier fluid. This embodiment may be achieved through the use of a configuration such as that shown in FIG. 19. Further, the DNA probe material may have more than a single fluorescent dye attached and the dyes may be of different intensities.

In both the testing of the biofluid through doping of the carrier fluid, and by tagging the DNA probes, the standard emissions output which will be expected to be detected, are obtained through controlled experimentations prior to implementation of the quality assurance processes.

Marking the biological material such as a DNA strand, will cause a shift in the frequency wavelength dependent on the amount of molecules which become attached to the DNA strand. Knowing what amount of material will result in a certain shift, can be used to determine the amount of biological material which has been ejected. When the shift is more or less than expected, this will indicate that the ejector was under or overloaded with the biological material, or that the drop ejector may not be functioning properly.

In a preferred embodiment, the biological material which will be included in the biological assay are single strand DNA. It is this DNA which will be tested against unknown DNAs.

In an alternative embodiment small pieces of duplex strand of DNA are used as markers. By then adding a fluorescent dye, matched to the double strand of DNA, the dye will move into the rungs of the ladder, i.e. these are intercoagulating dyes. Such an action will cause a shift in the emission spectrum of the dye. This shift can be used to achieve a quality assurance advantage by including a fixed piece of the double strand in all ejectors for additional quality control checks.

In a further embodiment, the dye markers may be configured and tagged to the biological material to provide altered signals dependent upon the age of the biological material. In this way, outdated biological material may be recognized and discarded.

While the foregoing discussion has centered on fluorescent dyes as the markers, other markers may also be used which provide the quality assurance verifications required for the present invention.

It is to be understood that while the figures in the above description illustrate the present invention, they are exemplary only. Others will recognize numerous modifications and adaptations of the illustrated embodiments which are in accord with the principles of the present invention. Therefore, the scope of the present invention is to be defined by the appended claims.

Having thus described the preferred embodiments, what is claimed is:

1. A method of providing a quality assurance check to a biological assay printed on a substrate, using a multi-ejector system having a plurality of individual drop ejectors, the method of providing a quality assurance check comprising:

loading drop ejectors of the multi-ejector system with a variety of biofluids, the biofluids including a carrier fluid, a biological material and at least one marker;

storing expected signature output signals for the biofluid loaded in the drop ejectors;

printing the biological assay consisting of drops from the biofluid loaded in the drop ejectors;

scanning the drops of the biological assay with a scanner capable of detecting the markers;

obtaining signature output signals for the drops of the biological assay;

comparing the obtained signature output signal for a specific drop and the expected signature output signal for the biofluid loaded in the drop ejector which ejected the specific drop; and verifying proper loading of the biofluids, proper storage of the expected signature output signals and proper placement of the biofluid drop, when the comparing step results in a desired correlation between the expected signature output and the obtained signature output.

2. The method according to claim 1 further including using a combination of markers in one biofluid loaded in one drop ejector.

3. The method according to claim 1 wherein the biological material is at least one of single strand DNA and duplex strand DNA.

4. The method according to claim 1 wherein the markers are fluorescent dye markers.

5. The method according to claim 1 wherein the drop ejectors are at least one of piezoelectric drop ejectors and acoustic drop ejectors.

6. The method according to claim 1 wherein the scanner is capable of detecting fluorescent dye markers.

7. The method according to claim 1 further including attaching a marker to the biological material.

8. The method according to claim 1 further including the markers being supplied in at least two different volumes.

9. A method of printing a biological assay on a substrate, using a multi-ejector system having a plurality of individual drop ejectors, the method comprising:

loading drop ejectors of the multi-ejector system with a variety of biofluids, the biofluids including a carrier fluid, a biological material and a combination of fluorescent dyes, and the drop ejectors being one of piezoelectric drop ejectors and acoustic drop ejectors;

storing expected signature output signals for each biofluid loaded in each of the drop ejectors;

selectively ejecting biofluid drops from selected ones of the drop ejectors in a pattern to form a biological assay;

scanning the drops of the biological assay with a scanner capable of detecting multiple signature output signals of the fluorescent dyes in the scanned drops;

obtaining the signature output signals for the drops of the biological assay, wherein each drop will have multiple signature output signals corresponding to the fluorescent dyes included in the biofluid drop;

comparing the obtained signature output signals for a specific drop and the expected signature output signals for the biofluid loaded in the drop ejector which ejected the specific drop, the expected signature output signals being pre-tested standardized signals; and verifying proper loading of the biofluids, proper storage of the expected signature output signals and proper placement of the biofluid drop, when the comparing step results in a desired correlation between the expected signature output and the obtained signature output.

10. The method according to claim 9 wherein the biological material is at least one of single strand DNA and duplex strand DNA.

11. The method according to claim 9 wherein the scanner is capable of detecting fluorescent dye markers.

12. The method according to claim 9 further including the markers being supplied in at least two different quantities.

* * * * *